United States Patent [19]

Oka et al.

[11] Patent Number: 4,778,882

[45] Date of Patent: Oct. 18, 1988

[54] METHOD OF CARRYING OUT CHEMICAL DEHYDRATION REACTION AND AN APPARATUS THEREFOR

[75] Inventors: Youichi Oka; Masao Yokoyama; Toshiaki Dairaku, all of Hikari, Japan

[73] Assignee: Takeda Chemical Industries, Ltd., Osaka, Japan

[21] Appl. No.: 788,433

[22] Filed: Oct. 17, 1985

[30] Foreign Application Priority Data

Oct. 19, 1984 [JP] Japan ................................ 59-220921

[51] Int. Cl.⁴ ........................ C07H 9/04; C07C 41/56
[52] U.S. Cl. ........................................ 536/124; 203/28
[58] Field of Search .......................................... 536/124

[56] References Cited

U.S. PATENT DOCUMENTS

| | | | |
|---|---|---|---|
| 2,426,968 | 9/1947 | Grubb ................................ | 260/488 |
| 3,290,263 | 12/1966 | Smythe et al. ...................... | 536/124 |
| 3,300,473 | 1/1967 | Christoffel et al. ................. | 536/124 |
| 3,598,804 | 8/1971 | Hindley et al. .................... | 536/124 |
| 3,607,862 | 9/1971 | Jeffe et al. ........................ | 536/124 |
| 4,460,767 | 7/1984 | Matsumura et al. ................ | 536/124 |
| 4,561,941 | 12/1985 | Dinnage ............................ | 203/24 |
| 4,659,808 | 4/1987 | Matsumura ........................ | 536/124 |

FOREIGN PATENT DOCUMENTS

A-091223 10/1983 European Pat. Off. .

Primary Examiner—Ronald W. Griffin
Attorney, Agent, or Firm—Wenderoth, Lind & Ponack

[57] ABSTRACT

An apparatus and a method for carrying out the dehydration reaction to produce a high boiling compound comprises charging a raw material and an organic solvent into a circulating system including a reactor, a preheater and an evaporator to cause the chemical dehydration reaction, drawing water, formed as a result of the dehydration reaction, together with the solvent in the form of vapor, compressing the vapor, effecting a heat exchange between the compressed vapor and the evaporator, dehydrating the compressed vapor by condensation, removing the dehydrated water out of the system, and returning the remaining solvent to the reactor.

4 Claims, 3 Drawing Sheets

METHOD OF CARRYING OUT CHEMICAL DEHYDRATION REACTION AND AN APPARATUS THEREFOR

BACKGROUND OF THE INVENTION

This invention relates to a method of and an apparatus for carrying out a chemical reaction involving dehydration in an industrially advantageous manner.

Among organic chemical reactions, there are known a number of reactions involving the formation of water, namely dehydration reactions, such as ketal formation, esterification and alcoholate formation.

In the dehydration reaction system, there exists an equilibrium between the starting material system and the reaction product system. Under the influence of water formed as the reaction proceeds, the progress of the reaction gradually slows down until an equilibrium is reached and the reaction does not proceed any more.

Thus, the equilibrium generally renders it difficult to obtain the desired main products in high yields in the dehydration reaction system.

For this reason, the art has thus far contrived to increase the yields of reaction products by using a reaction solvent in large amounts to thereby dilute relatively the concentration of water formed and thus reduce the influence of the equilibrium on the reaction, by using a variety of dehydrating agents inert to the reaction to thereby remove the water formed out of the system, or by repeating batchwise charging of a reaction solvent and water removal by distillation to thereby decrease the concentration of water formed and reduce the influence of water step by step.

The law of equilibrium teaches that an increase in the yield of a desired main reaction product can be expected when a component of the starting material system, for instance a reaction solvent, is used in a relatively increased amount. This measure, however, cannot be advantageous from the industrial viewpoint since a large quantity of energy is required not only for carrying out the reaction but also for separation and recovery of the solvent after reaction.

Even when the water formed can be removed through the use of a variety of dehydrating agents, their general use is not an easy matter because considerable expenses are incurred for the regeneration or recovery of the dehydrating agents.

For obtaining the desired products in good yields on a commercial scale, it is therefore very important to conduct the reaction while removing the water formed in the dehydration reaction out of the reaction system efficiently.

SUMMARY OF THE INVENTION

The inventors studied intensively to obviate the above problems and, as a result, have now completed the present invention.

Thus, the invention is to provide a method of and an apparatus for carrying out a chemical dehydration reaction to give a high boiling compound using an organic solvent, which method comprises conducting the reaction while distilling off the resulting water together with the organic solvent by means of a vapor recompression technique.

The apparatus according to the present invention is featured in that it comprises a reactor for accommodating a raw material and an organic solvent and for effecting a chemical dehydration reaction to produce a high boiling compound; a preheater for drawing a reaction product from the reactor and for heating the reaction product; an evaporator for receiving the reaction product from the preheater and for evaporating together with the organic solvent a water formed by evaporating the reaction product under reduced pressure, while returning the resultant high boiling compound to the reactor; a blower for drawing vapor from the evaporator and for compressing the vapor to elevate its temperature; a heat exchanging passage integrally provided in the evaporator for receiving the compressed vapor from the blower for the heat exchange with the reaction product within the evaporator to facilitate said evaporation; a dehydrator for condensing the compressed vapor fed from the heat exchanging passage to dehydrate and for discharging water so dehydrated; and a return passage for returning to the reactor the organic solvent which has been dehydrated in the dehydrator.

Also, according to the present invention, a method for carrying out the dehydration reaction to produce the high boiling compound by the use of the above described apparatus comprises charging the raw material and the organic solvent into the circulating system including the reactor, the preheater and the evaporator to cause the chemical dehydration reaction, drawing the water, formed as a result of the dehydration reaction, together with the solvent in the form of vapor, compressing the vapor by the use of a blower, effecting a heat exchange between the compressed vapor and the evaporator to increase the rate of heat exchange, dehydrating the compressed vapor by condensation with the use of the dehydrator, removing the dehydrated water out of the system, and returning the remaining solvent to the reactor. With this method, by repeating the process cyclically, the organic solvent can be used for the subsequent reactions while the formed water is removed.

The present invention is applicable to any chemical dehydration reaction in which water is formed intermolecularly and the desired product is a high boiling compound, without any particular limitation. The term "high boiling compound" as used herein means a compound which does not boil at the reaction temperature and has a boiling point higher than that of the organic solvent used such that it cannot be distilled off together with said organic solvent.

The chemical dehydration reaction includes, among others, ester formation from an acid, such as a carboxylic acid, a sulfonic acid or an inorganic acid, and an alcohol, alcoholate formation from an alkali metal hydroxide (e.g., potassium hydroxide, sodium hydroxide) and an alcohol, and acetal or ketal formation as a result of condensation of a carbonyl compound (aldehyde or ketone) with a hydroxy-containing compound.

A typical example of the ester formation is the production of diethyl maleate from ethanol and maleic acid, and a typical example of the alcoholate formation is the production of sodium methylate from methanol and caustic soda. Examples of the acetal or ketal formation are the formation of acetals from an aldehyde and an alcohol and the formation of ketals by condensation of two hydroxy groups of a polyhydroxy compound (e.g., sugar, 2-keto-gluconic acid, ascorbic acid) and one molecule of a ketone compound (Japanese Laid-open Patent Publication Nos. 58-55494 and 58-167582, both published in 1983, and Japanese Patent Application Nos. 58-179872, 58-179873 and 58-181305, all filed in 1983 in Japan.)

The organic solvent to be used in carrying out a chemical dehydration reaction in accordance with the invention may be any solvent capable of being distilled off together with water in said reaction. It may be a starting compound simultaneously serving as a solvent, or a solvent irrelevant to desired product formation but used merely for dissolving starting materials. An appropriate organic solvent species is to be selected depending on the reaction to be conducted. Generally, however, there may be mentioned such common solvents as alcohols (e.g., methanol, ethanol, propanol, isopropyl alcohol), ketones (e.g., acetone, methyl ethyl ketone, diethyl ketone, cyclohexanone, methyl isobutyl ketone) and, further, aromatics (e.g., benzene, toluene, xylene). In carrying out the invention, a higher proportion of water in the gaseous phase is advantageous from the industrial standpoint in distilling off water formed together with the organic solvent. For this reason, it is desirable to use an organic solvent capable of forming an azeotrope with water provided that the solvent does not defeat the purpose of the reaction. Examples of such azeotropic system are systems of water, on one hand, and, on the other, benzene, ethanol, and methyl isobutyl ketone.

The reaction conditions such as temperature, pressure and time are suitably selected depending on the nature of the chemical dehydration reaction to be conducted. In this respect, there is no particular limitation in carrying out the invention. For catalyzing the chemical dehydration reaction, various acid catalysts which are in in general use may be used provided that they do not cause any trouble in using the method of the invention. For ketal formation, for instance, there may be mentioned such catalysts as cupric chloride or bromide described in Japanese Laid-open Patent Publication No. 58-55494, published in 1983, copper or iron, or an oxide, hydroxide or salt thereof and hydrogen halide, which are described in Japanese Laid-open Patent Publication No. 58-167583, published in 1983, catalysts defined as hydrogen iodide in Japanese Laid-open Patent Publication No. 58-167582, published in 1983 (iodine, hydroiodic acid, etc.) and, further, antimony pentachloride and antimony pentafluoride. Examples of the esterification catalyst are sulfuric acid, hydrochloric acid and paratoluenesulfonic acid.

In carrying out the method of the invention, the water formed and the organic solvent are distilled off in a vapor recompression system wherein the vapor generated in an evaporator is recompressed for utilization as a source of heat for itself.

The extent of compression in said vapor recompression is selected depending on the elevation of boiling point in the reaction system, the mechanical efficiency in vapor compression, and other factors. Generally, however, a compression of not more than about 2, for example, about 1.4 to 1.6, is preferable in most cases.

BRIEF DESCRIPTION OF THE DRAWINGS

This and other objects and features of the present invention will become clear from the following description taken in conjunction with preferred embodiments thereof with reference to the accompanying drawings, in which.

DETAILED DESCRIPTION OF THE EMBODIMENTS

Figure 1:
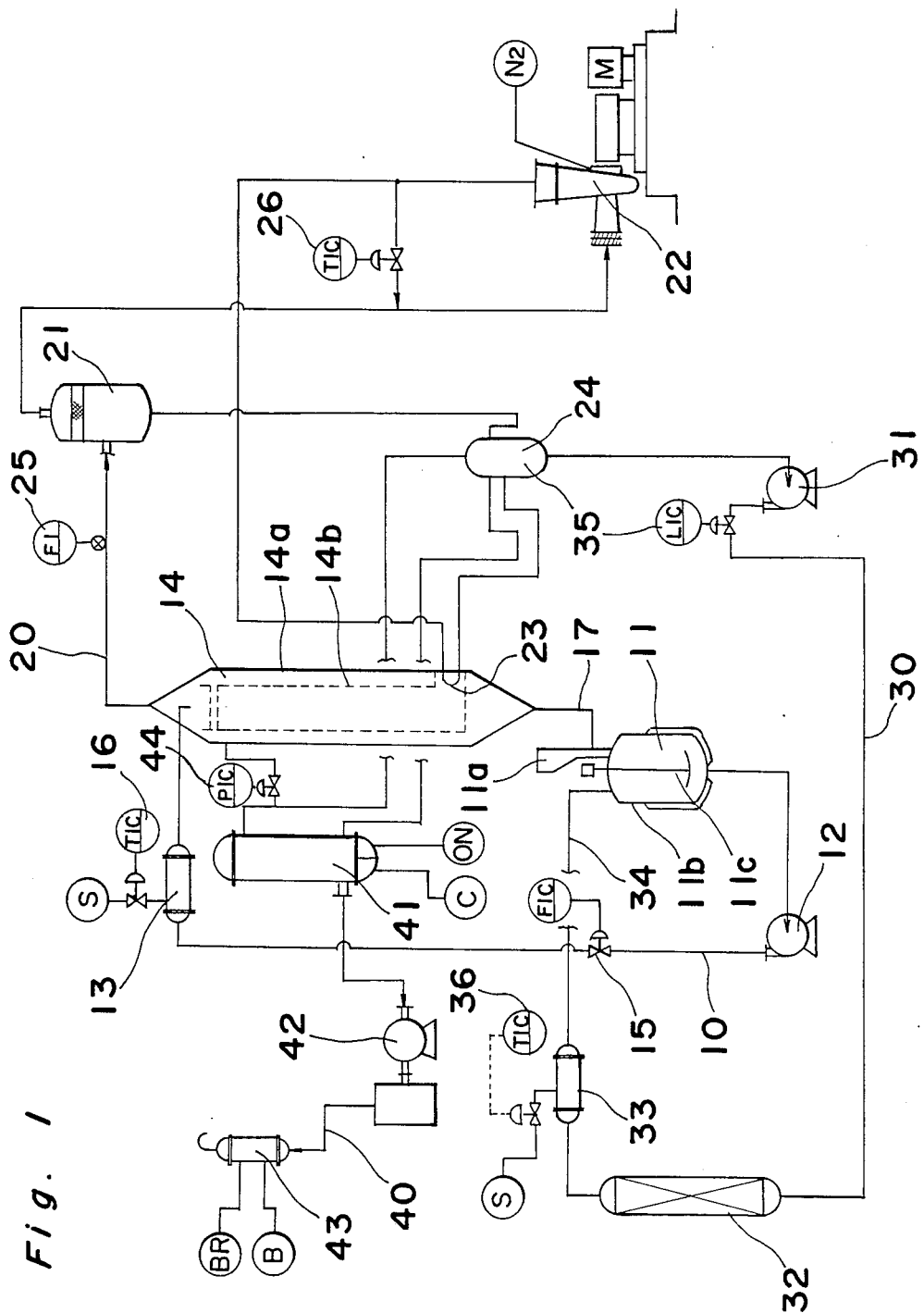
FIGS. 1 to 3 are system diagrams of an apparatus required to carry out a chemical dehydration reaction according to different embodiments of the present invention.

Before the description of the present invention proceeds, it is to be noted that like parts are designated by like reference numerals throughout the accompanying drawings.

Referring to FIG. 1, an apparatus for carrying out the dehydration reaction shown therein comprises a reaction circulating system comprised of a loop circuit 10 having a reactor 11, a circulating pump 12, a vapor preheater 13 and an evaporator 14; a heat exchanger system comprised of a line circuit 20 having a gas-liquid separator 21 communicated with the evaporator 14, a blower 22, a heat exchanging passage 24, and a condensate tank 24; a combined dehydration and solvent return system comprised of a line circuit 30 having a condensate pump 31, a dehydrator 32, liquid preheater 33 and a return passage 34 all disposed between the evaporator 14 and the condensate tank 24; and a vacuum generating system comprised of a line circuit 40 having a condensor 41 communicated with the evaporator 14, a vacuum pump 42 and a vent condensor 43. The reaction circulating system is provided with a flow control valve 15, and a temperature control valve 16. The heat exchanger system is provided with a flow indicator 25 and a temperature control valve 26. The combination dehydration and solvent return system is provided with a combined level indicator and control valve 35 and a temperature control valve 44. The vacuum generating system is provided with a pressure control valve 44.

The reactor 11 is so designed and so operable that, when a raw material and a solvent are introduced into a tank 11b and are then mixed together by a stirrer 11c, a chemical dehydration reaction necessary to obtain a high boiling compound can be caused to take place, the resultant reaction product being, while heated by the vapor preheater 13, supplied by the circulating pump 12 to the evaporator 14. The evaporator 14 is so designed and so operable that, while the reaction product is allowed to recyclically flow downwards from above within a tank 14a, the reaction product can be allowed to evaporate in contact with a radiator panel 14b disposed inside the tank 14a. Evaporation of the reaction product is carried out by reducing the internal pressure inside the tank 14a of the evaporator 14 by means of the vacuum generating system and, at the same time, by effecting the heat exchange at the radiator panel 14b inside the tank 14a with vapor of the heat exchange system. A vapor produced from the evaporator 14 is supplied from the top of the tank 14a to the gas-liquid separator 21 and, on the other hand, the resultant high boiling compound is returned from the bottom of the tank 14a to the reactor 14 through a return passage 17. This evaporator 14 is preferably of such a structure that scales of a reaction liquid will not be formed on the radiator panel 14b and, at the same time, no bias will occur in the concentration of a catalyst and other reaction liquid at the radiator panel 14b so that the amount of the reaction liquid circulated can be increased. For example, where the reaction liquid is in the form of a slurry or scale, the evaporator 14 is preferred to be of a plate type, or otherwise, it is preferred to be of a tube or plate type. The gas-liquid separator 21 serves to protect the blower 22 from mist of a highly corrosive material, such as catalyst contained in the reaction liquid, which will be passed through the blower 22. The blower 22 serves to supply a vapor from the gas-liquid separator 21 into the heat exchanging passage 23. The heat exchanging passage 23 is provided integrally with the evaporator 14 and is so operable that heat exchange can take place through the radiator panel 14b inside the tank 14a between the product formed in the evaporator 14 and the vapor within the heat exchanging passage 23. In other words, the heat exchanging passage 23 is so operable that heat energy evolved in the vapor within the heat exchanging passage 23 can be imparted through the radiator panel 14b to the product formed in the evaporator 14 to facilitate evaporation of the product within the evaporator 14.

The vapor having passed through the heat exchanging passage 23 is collected in the condensate tank 24. The condensate tank 24 collects the mist in the separator 21, the vapor in the heat exchanging passage 23 and mist in the condenser 41 of the vacuum generating system and from which tank 24 is supplied the collected liquid solvent, containing water, towards the dehydrator 32 by means of the condensate pump 31. Within the dehydrator 32, the water-containing solvent supplied from the condensate pump 31 is allowed to pass through a dehydrating agent such as, for example, anhydrous Glauber's salt ($Na_2SO_4$), zeolite or the like to provide a hydrated solvent which is subsequently drawn out of the system whereas the solvent is circulated to the reactor 11 through the preheater 33 and the return passage 34, thereby completing a cycle. By repeating the above described cycle, water formed upon the chemical dehydration reaction occurring in the reactor 11 between the raw material and the organic solvent can be dehydrated, leaving the high boiling compound of high purity.

The vacuum pump 42 is operable to draw the air within the evaporator 14 through the condenser 41 to maintain the pressure inside the evaporator 14 at a constant value. The air discharged from the vacuum pump 42 is discharged out of the system through the vent condenser 43.

When the apparatus of the above described construction is to be used, for example, 500L of anhydrous aceton and 50 kg of sorbose are charged into and mixed within the reactor 11 into which 0.6 kg of HI (57%) is charged. Subsequently, the vacuum pump 42 is operated at, for example, 30 m$^3$/H to reduce the pressure inside the evaporator 14 to a value within the range of 500 to 515 Torr. The vapor preheater 13 is activated to heat the vapor drawn by the blower 22 to 46° C. and, at the same time, the blower 22 is operated, and the degree of vacuum, the temperature, the liquid level, and the flow rate in the system are controlled. The apparatus causes chemical dehydration for a predetermined time, for example, about 12 hours, under a predetermined standard condition. The standard condition is such that, by way of example, the reduced pressure is within the range of 500 to 515 Torr; the temperature inside the reactor is 46 ±2° C.; the inlet temperature of the evaporator 14 is 45.9° C.; the temperature of the vapor as removed from the evaporator 14 is 44.4° C.; the temperature of the formed product as removed from the evaporator 14 is 45.3° C.; the temperature inside the heat exchanging passage 23 is 52.9° C.; and the quantity of anhydrous aceton supplied is 500 kg/H.

As hereinbefore described, according to the present invention, the reactant charge containing at least one organic solvent is introduced into the reactor 11 and the reaction mixture is recycled via the evaporator 14 by means of the circulating pump 12.

At the initial stage of operation, steam, for instance, is fed to the jacket of the evaporator 14 through the preheater 13 to thereby raise the temperature of the recycling liquid gradually, whereupon the reaction starts and part of the organic solvent and part of the eater formed begin to evaporate together. The vapor amount gradually increases and the separator 21 and the blower 22 are heated. When the temperature rise has reached a sufficient level to enable the blower 22 to operate, the supply of steam is discontinued, whereby the arrangement shown in FIG. 1 ordinarily begins to function as a reactor and evaporator of the vapor recompression type and keep the reaction proceeding. This vapor is a mixed vapor containing water in the organic solvent. The water content, which varies depending on the kind of dehydration reaction, the reaction conditions, the state of reaction and so forth, is generally about 200 to 5,000 ppm and, when an azeotropic system is formed, said water content can be increased to a level above said range.

This vapor is then subjected to gas-liquid separation in the separator 21, and then pressurized in the blower 22, which is of the Roots type or of the turbo type, for instance. The vapor, now with an increased enthalpy, is fed to the jacket portion of the evaporator 14, forming the heat exchanging passage 23, to supply heat to the liquid reaction mixture, and then transferred, as a drain, to the dehydrator 32 through the condensate pump 31.

The reaction is continued in a stable state by supplying the organic solvent in an amount corresponding to the decrease caused by evaporation to the reactor 11 via the condensate pump 31, the dehydrator 32, the preheater 33 and the return passage 34. The inert gas involved in the reaction conditions is discharged by means of the vacuum pump 42. As that portion of the organic solvent which is to be supplied for supplementation, that portion treated in the above-mentioned dehydrator 32 is used repeatedly with advantage from the reaction process viewpoint.

With regard to the vapor recompression type evaporation equipment to be used in the practice of the method of the invention, various combinations are possible with respect to the kind, type and so forth.

As for the evaporator, for instance, this may appropriately be selected from among various types such as the plate type and tubular type and the reaction mixture-recycling method from among the forced, spontaneous flowing down and other modes, in due consideration of the character of the reaction and the physical properties of the reaction mixture, among others. It is also possible to adjust the concentration of the reaction mixture and/or the rate of reaction by increasing or decreasing the amount of the organic solvent to be fed.

Figure 2:
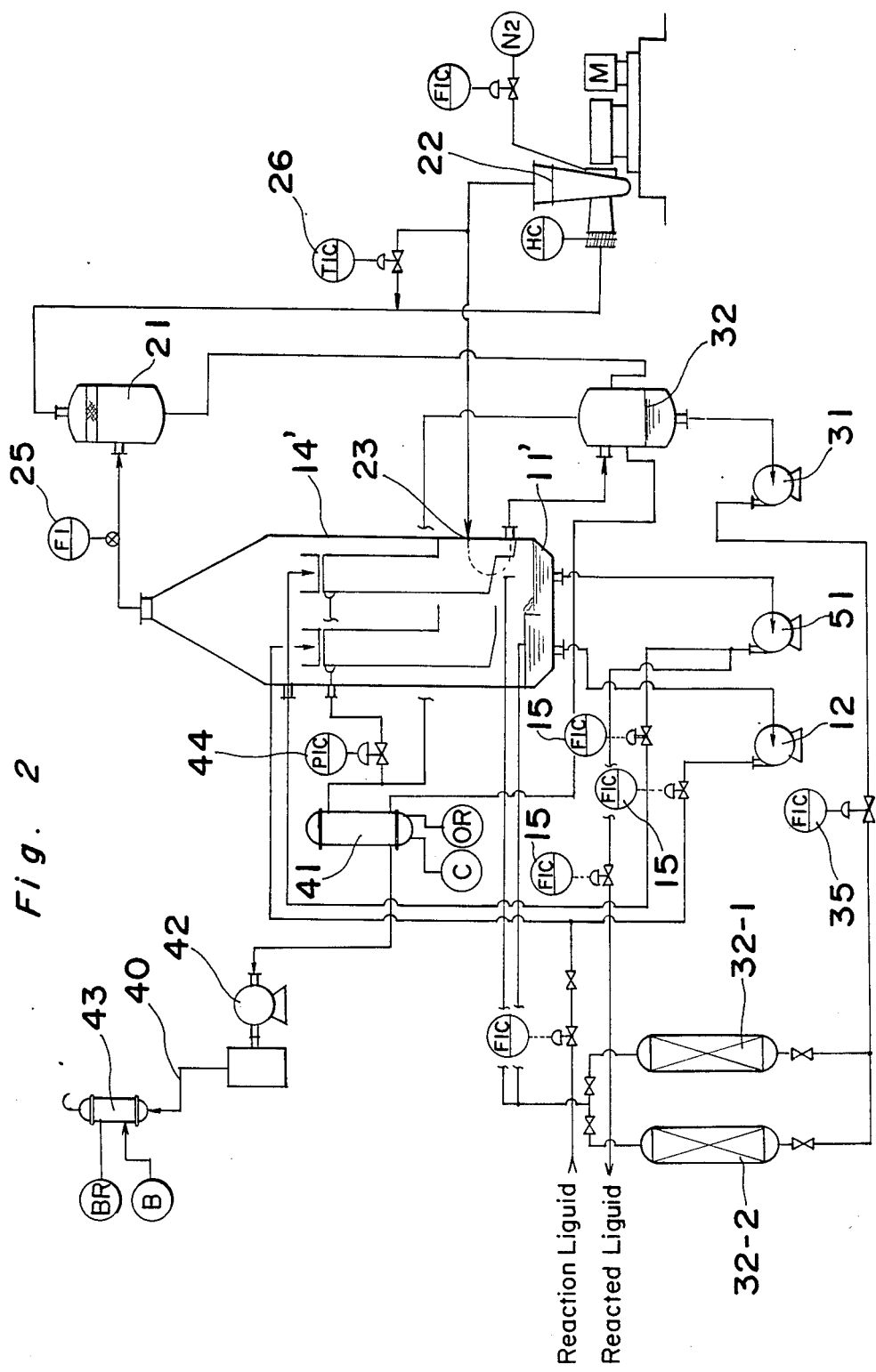
Figure 3:
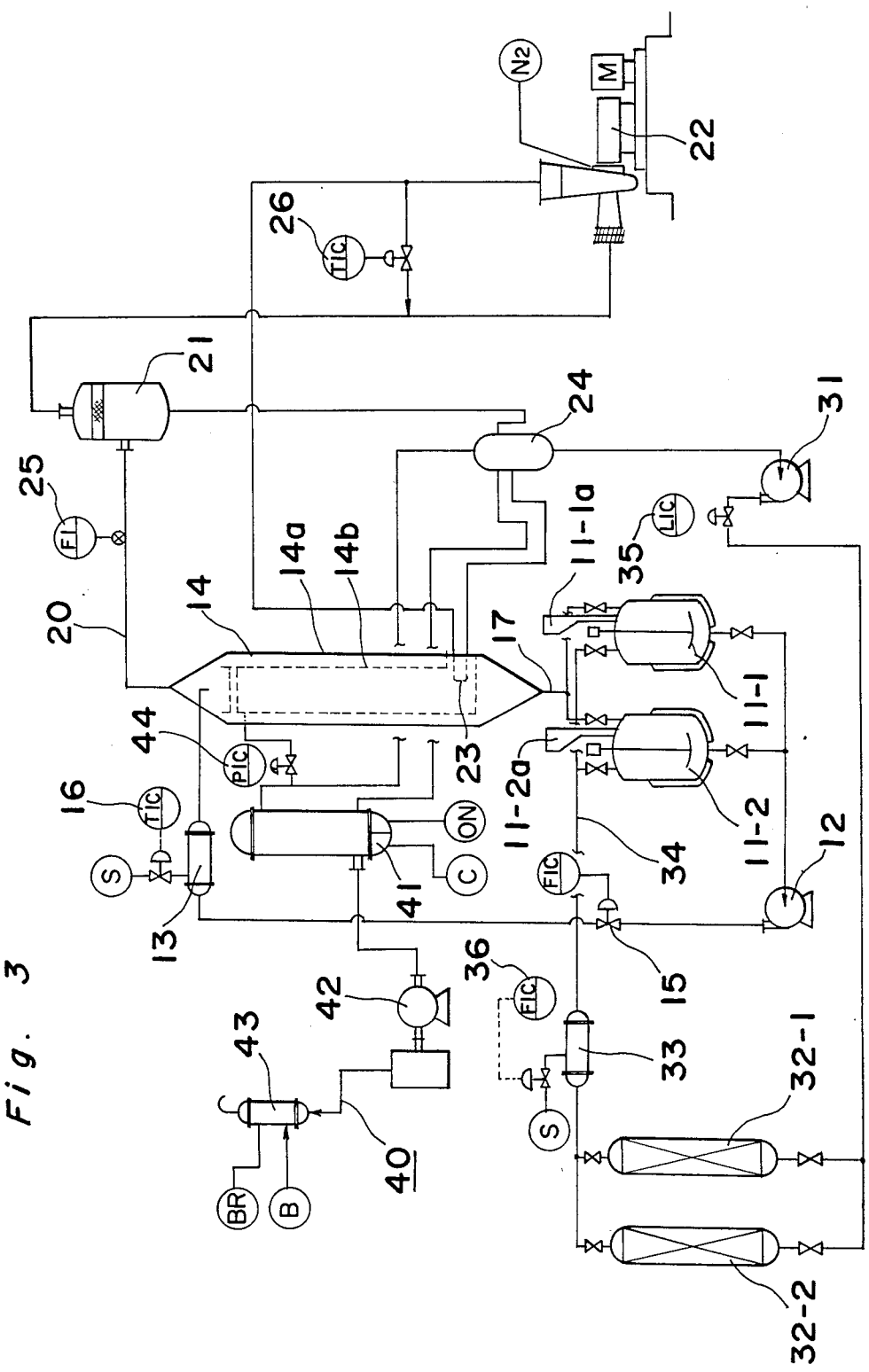

The invention can be carried out either continuously by drawing the reaction mixture out of the reaction system from the bottom of the reactor through a circulating and drawings pump 51 while continuing the reaction as shown in FIG. 2, or batchwise by arranging a plurality of reactors 11-1 and 11-2 in parallel relationship to each other as shown in FIG. 3, as selected depending on the characteristics of the reaction system and/or equipments. It is to be noted that in the apparatus shown in FIG. 2, the reactor 11' is integrally formed with the evaporator 14'.

Hereinafter, the invention will be illustrated by way of examples which are not intended to limit the scope of the invention, but are provided only for the purpose of illustration.

EXAMPLE 1

To 700 liters of actetone, there were added 50 kg of L-sorbose and 1.1 kg of hydroiodic acid (57%), and the reaction was conducted at 51° C. for 6 hours. For this reaction, there was used an apparatus composed of a reactor, a plate type evaporator and a compressor as connected in such a manner as to give a vapor recompression type evaporation system, as shown in FIG. 1. At the initial stage of the reaction, the evaporator was heated by feeding external steam thereto at 1.9 kg/cm$^2$ (gauge). As a result, the plate inside temperature reached about 60° C. in about 70 minutes, namely a steady operational state. Thereafter, aqueous acetone (water content: 200 to 3,000 ppm) was distilled off at a rate of about 700 liters/hour and treated for dehydration with anhydrous sodium sulfate. The dried acetone thus obtained was maintained at 51° C. and fed to the reactor for compensation for that portion of acetone which was being distilled off. In this manner, the reaction was continued.

After completion of the reaction, the reaction mixture was cooled and neutralized and the acetone was then distilled off. The residue was extracted with benzene and the benzene was distilled off from the extract, and there was obtained 60.5 kg (84% yield) of 2,3:4,6-di-O-isopropylidene-L-sorbofuranose as a residue. The utilities required of the method of this invention are shown in Table 1 in comparison with those for a prior art simple distillation method.

TABLE 1

|  | Simple distillation method | Method of invention |
|---|---|---|
| External steam (kg/hr) | 140 | 11 |
| Electric power (kWH/hr) | — | 4.0 |

EXAMPLE 2

50 kg of L-Sorbose and 0.6 kg of hydroiodic acid (57%) were added to 500 liters of acetone, and the reaction was carried out at about 46° C. in the same manner and in the same equipment as in Example 1. The evaporator was heated by feeding external steam thereto at 1.9 kg/cm$^2$ (gauge). The plate inside temperature reached about 55.5° C. in about 60 minutes, when aqueous acetone (water content: 300 to 2,000 ppm) began to distill off at a rate of 500 kg/hour. The aqueous acetone was dehydrated with anhydrous sodium sulfate and fed at 46° C. to the reactor for compensation of the decrement of acetone due to distilling off. The reaction was continued in this manner for 12 hours.

The reaction mixture was treated in the same manner as in Example 1 to give 63.5 kg (88% yield) of 2,3:4,6-di-O-isopropylidene-L-sorbofuranose. The utility consumptions in this example are shown in Table 2 in comparison with a conventional simple distillation case.

TABLE 2

|  | Simple distillation method | Method of invention |
|---|---|---|
| External steam (kg/hr) | 120 | 10 |
| Electric power (kWH/hr) | — | 3.7 |

EXAMPLE 3

To 500 liters of ethanol, there were added 150 kg of maleic anhydride and 4.5 kg of concentrated sulfuric acid, and the reaction was conducted in the same equipment as used in Example 1 at about 64° C. for 7 hours. From the beginning of the reaction, steam was fed to the evaporator at 1.9 kg/cm$^2$ (gauge). In 80 minutes, the reactor inside temperature reached a steady level of about 74° C. The ethanol was distilled off together with the water formed.

For compensating that amount of ethanol which had been distilled off, an average of 300 liters/hour of dehydrated ethanol was continuously fed while preheating the same at 64° C. After completion of the reaction, the ethanol and so on were distilled off by heating. There was obtained 210 kg (95% yield) of diethyl maleate as a residue. The utility consumptions in this example are shown in Table 3 in comparison with a conventional simple distillation method.

TABLE 3

|  | Simple distillation method | Method of invention |
|---|---|---|
| External steam (kg/hr) | 94 | 6 |
| Electric power (kWH/hr) | — | 2.4 |

EXAMPLE 4

10 kg of caustic soda was added to 400 liters of methanol, and the reaction was conducted at about 55° C. in the same reaction/evaporation equipment as mentioned in Example 1. For initiating the reaction, steam was fed to the evaporator at 1.9 kg/cm$^2$ (gauge), whereby the plate inside temperature gradually increased to about 65.5° C. and methanol with a water content of 0.7% began to distill off at that temperature. In this steady state of reaction, aqueous methanol was distilled off at 200 liters/hour on an average and the corresponding dehydrated methanol was fed continuously at 55° C. After completion of the reaction, the solvent and volatiles were distilled off and there was obtained 16.5 kg (98% yield) of sodium methylate as a residue. The utility consumptions in this method are shown in Table 4 in comparison with a conventional simple distillation method.

TABLE 4

|  | Simple distillation method | Method of invention |
|---|---|---|
| External steam (kg/hr) | 82 | 4 |
| Electric power (kWH/hr) | — | 1.5 |

As hereinbefore described, according to the present invention, the water formed in the chemical dehydration reaction is distilled off together with the organic solvent by way of vapor recompression. As a result, the water formed can be eliminated from the reaction system efficiently and the chemical equilibrium can be shifted rapidly.

More specifically, according to the present invention, the reaction is caused to proceed by continuously pouring the dehydrating solvent while the water is distilled off from the system together with the solvent. The use of the vapor recompression device for the reaction liquid of solvent system has first made the method of the invention practically acceptable from the viewpoint of economics. Hitherto, a substantial quantity of strong acid catalyst such as sulfuric acid has been used in a chemical synthesis of diacetone-L-sorbose (DAS). Although the use of an increased quantity of solvent brings about the increased diluting effect of the formed water, the amount of the solvent that can be limited in terms of the securement of the catalyst concentration and the cost required to recover the solvent, and according, the DAS yield in the DAS reaction is as follows:

| | | | |
|---|---|---|---|
| Prior Art | ( L-sorbose 50 Kg<br>Acetone 700 L<br>$H_2SO_4$ 26.5 L ) | DAS Yield: 80% |
| Invention | | DAS Yield: 88% |

Thus, while the prior art has required the use of a complicated and expensive recovering process for an intermediate product which has not resulted in DAS, the present invention is successful in eliminating the use of such a recovery process.

The invention thus provides a method of carrying out a chemical dehydration reaction in a very advantageous manner from the industrial standpoint, by which method the yield of the desired product can be increased at a saving of energy through positive application of an evaporation equipment of the vapor recompression type for the purpose of shifting the reaction equilibrium to the reaction product side.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. A method for carrying out a chemical dehydration reaction to give a high boiling compound using an organic solvent, said organic solvent being one which is capable of being distilled off with said resulting water and said solvent being a starting material, or one serving as a solvent for the starting materials, which method comprises conducting the reaction while distilling off the resulting water together with the organic solvent by way of a vapor recompression technique by using the following apparatus which comprises:

a reactor for accommodating a raw material and an organic solvent and for effecting a chemical dehydration reaction to produce a high boiling compound;

a preheater for drawing a reaction product from the reactor and for heating the reaction product;

an evaporator for receiving the reaction product from the preheater and for evaporating together with the organic solvent, water formed by evaporating the reaction product under reduced pressure, while returning the resultant high boiling compound to the reactor;

a blower for drawing vapor from the evaporator and for compressing the vapor to elevate its temperature;

a heat exchanging passage integrally provided in the evaporator for receiving the compressed vapor from the blower for the heat exchange with the reaction product within the evaporator to facilitate said evaporation;

a dehydrator for condensing the compressed vapor fed from the heat exchanging passage to dehydrate and for discharging water so dehydrated; and a return passage for returning to the reactor the organic solvent which has been dehydrated in the dehydrator.

2. The method as claimed in claim 1, wherein the water content in the organic solvent is about 200 to 5,000 ppm.

3. The method as claimed in claim 1, wherein the chemical hydration reaction is a reaction of a ketone with a sugar to produce a sugar ketal.

4. The method as claimed in claim 1, wherein the chemical hydration reaction is a reaction to producing diacetone-L-sorbose.

* * * * *